United States Patent [19]
Uenoyama et al.

[11] Patent Number: 5,856,117
[45] Date of Patent: Jan. 5, 1999

[54] METHOD FOR MEASURING THE CONCENTRATION OF PROTEASE INHIBITORS, KIT FOR USE IN SUCH A METHOD AND METHOD FOR DISSOLVING A SUBSTRATE

[75] Inventors: Harumi Uenoyama, Osaka; Kyouichi Ohshiro, Kyoto; Atsuko Nanbu, Shiga; Satoshi Fukunaga, Osaka, all of Japan

[73] Assignee: Kyoto Daiichi Kagaku Co., Ltd., Kyoto, Japan

[21] Appl. No.: 879,962

[22] Filed: Jun. 20, 1997

[30] Foreign Application Priority Data

Jun. 21, 1996 [JP] Japan ................................. 8-162163
Jun. 26, 1996 [JP] Japan ................................. 8-166311

[51] Int. Cl.$^6$ .............................. C12Q 1/37; C12Q 1/00; G01N 33/53
[52] U.S. Cl. ................................ 435/23; 435/24; 435/4; 435/963; 435/183; 435/975
[58] Field of Search .................................. 435/23, 24, 4, 435/963, 183, 975

[56] References Cited

U.S. PATENT DOCUMENTS 5,354,491  10/1994  Bjorkquist et al. ........................ 435/23

FOREIGN PATENT DOCUMENTS 0 168 738  1/1986  European Pat. Off. .
0 216 179  4/1987  European Pat. Off. .
7-155198   6/1995  Japan .
1160311    6/1985  U.S.S.R. .

OTHER PUBLICATIONS

H.J. Faarvang, "Excretion of Mingin in Urine in Normal and in Pathological Conditions", *Scandinav. J. Clin. & Lab. Investigation 17* (Suppl. 83), pp. 25–28, 1965.

"Measurement of Alpha$_1$–Antitrypsin in Serum, by Immunodiffusion and by Enzymatic Assay", *Clinical Chemistry*, vol. 20, No. 3, pp. 396–399, 1974.

Beatrice Kassell, "Bovine Trypsin–Kallikrein Inhibitor (Kunitz Inhibitor, Basic Pancreatic Trypsin Inhibitor, Polyvalent Inhibitor from Bovine Organs)", *Methods of Enzymatic Analysis*, 3rd Ed., vol. 10, pp. 844–845, 1970. Month not available.

Beatric Kassell, "Protoeolytic Enzyme Inhibitors from *Ascaris lumbricoides*", *Methods of Enzymatic Analysis*, 3rd Ed., vol. 10, pp. 872–873, 1970. Month not available.

Shiro Kuwajima, et al., "Urinary trypsin inhibitor and its clinical usefulness for diagnosis of acute phase reactant and renal disease", *Japanese Journal of Inflammation* Review Article, vol. 9, No. 3, pp. 175–182, May 1989.

Shiro Kuwajima, et al., "Automated Measurement of Trypsin Inhibitor in Urine with a Centrifugal Analyzer: Comparison with Other Acute Phase Reactants", *Clinical Biochemistry*, vol. 23, pp. 167–171, Apr. 1990.

T. Bogacheva et al., "Method for Determining the Molar Concentration of Protease Inhibitors and Their Enzyme Affinity", *Chemical Abstracts*, vol. 98, No. 5, p. 294 (Jan. 31, 1983).

European Search Report (Sep. 23, 1997).

*Primary Examiner*—Louise N. Leary
*Attorney, Agent, or Firm*—Merchant, Gould, Smith, Edell, Welter & Schmidt

[57] ABSTRACT

This invention provides a method for measuring the concentration of urinary trypsin inhibitors which is excellent in precision and reproducibility, whose operation is simple, and in which a possibility of damaging a plastic cell is eliminated. The method for measuring the concentration of urinary trypsin inhibitors comprises mixing an urine sample, a protease solution containing trypsin, and a buffer solution, adding a substrate solution to the mixture to cause the enzyme reaction, and measuring the activity of the enzyme, wherein the buffer solution is prepared so that it contains at least 0.15 μmol calcium per 1 μg of the trypsin but no more than 100 μmol calcium per 1 ml of the urine sample in the reaction mixture, and wherein the substrate solution is prepared by dissolving the substrate in an organic solvent and diluting the mixture solution with aqueous medium, wherein at least one of an amphoteric surfactant and a nonionic surfactant is added to at least one of the organic solvent and the aqueous medium.

36 Claims, 1 Drawing Sheet

METHOD FOR MEASURING THE CONCENTRATION OF PROTEASE INHIBITORS, KIT FOR USE IN SUCH A METHOD AND METHOD FOR DISSOLVING A SUBSTRATE

BACKGROUND OF THE INVENTION

This invention is related to a method for measuring the concentration of protease inhibitors, a kit for use in such a method and a method for dissolving a substrate.

Trypsin inhibitors in urine such as urinary trypsin inhibitor (UTI) have lately attracted considerable attention as an indicator for the condition of an organism, and research has been carried out in the field of clinical medicine. For example, it is known that UTI is found in urine in an organism when it is under internal or external stresses caused by inflammation, surgical operation, or the like ("The Clinical Importance of Urinary Trypsin Inhibitor and its clinical usefulness for diagnosis of acute phase reactant and renal disease" Shiro Kuwajima et al., JAPANESE JOURNAL OF INFLAMMATION REVIEW ARTICLE, VOL. 9, NO. 3, MAY 1989).

Because the inhibitory activity of the urinary trypsin inhibitor depends on the amount present, its concentration is evaluated by measuring the inhibited activity of trypsin. The measurement is carried out, for example, by mixing a urine sample, an enzyme (i.e. protease) solution containing trypsin, and a buffer solution, and then adding a substrate solution to the mixture and measuring the enzyme reaction.

In this measurement, benzoyl-arginine-p-nitroanilide (BAPNA) can be used as a substrate. However, because BAPNA is only slightly soluble in water, this substrate solution is prepared by dissolving BAPNA in dimethyl sulfoxide (DMSO) and then diluting the mixture about two-fold with water. Furthermore, calcium is normally used as a trypsin activation agent in this measurement, and it is usually mixed in the buffer solution.

However, there are problems, described below, in such a conventional method for measurement.

First, when the concentration of the calcium mixed in the buffer solution or the like is low, trypsin may be activated by the influence of calcium present in the urine sample, so that the observed trypsin activity measurement would indicate a lower value for the urinary trypsin inhibitor concentration than the real value. Furthermore, if an excess amount of calcium is added, it reacts with carbonate ions, phosphate ions and the like present in the urine to produce precipitates, which affect the measurement. Although pretreatment such as centrifugation or the like may be conducted to remove them, this may complicate the measurement.

Furthermore, an organic solvent such as DMSO may damage a plastic cell generally used in an automatic analytical apparatus, so that the amount of the organic solvent which can be used is limited. Accordingly, the amount of the substrate which can be dissolved in the organic solvent is also limited. As a result, the sensitivity of the measurement is difficult to improve, and the reproducibility is limited. Moreover, there is a possibility of trypsin activity being inhibited by using an organic solvent. In addition, the rather insoluble BAPNA can be dissolved by using an organic solvent, but if the amount used is not sufficient, there is a possibility of BAPNA crystallizing out of solution when the substrate solution is kept in long-term storage or in refrigeration. Therefore, in a conventional measuring method, when a slightly soluble substrate such as BAPNA is used with an organic solvent, it has been necessary to prepare a substrate solution at each measurement, and immediately thereafter provide it for the measurement.

SUMMARY OF THE INVENTION

Figure 1:
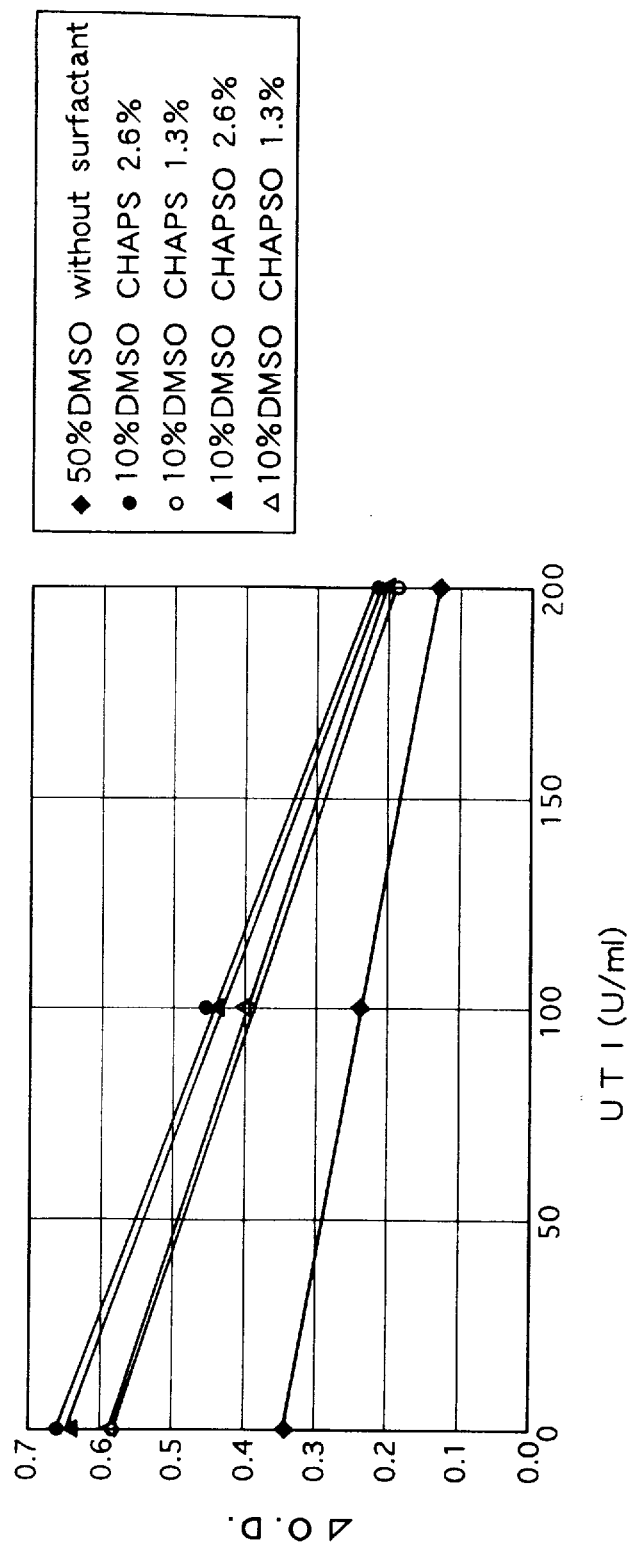
FIG. 1 is a graph of a calibration curve of UTI in an embodiment of the invention.

It is an object of the present invention to provide a method for measuring the concentration of protease inhibitors, which is excellent in precision and reproducibility, which requires simple operation, and further in which a possibility of damage to a plastic cell is eliminated. A kit for use in such a method, and a general improved method for dissolving a substrate are further objects of the present invention.

Essentially, an important aspect of the invention is based on using a surfactant, specifically an amphoteric and/or nonionic surfactant, to prepare the protease substrate solution which is used in the protease inhibitor assay. The surfactant (or surfactants) is (are) conveniently added to or included within one or both of the solvents used to prepare the substrate solution e.g. to the organic solvent or to the water used for dilution.

In one aspect, the invention thus provides a method for the assay of a protease inhibitor in a sample, comprising mixing the sample, a protease, calcium and a protease substrate, and assaying the content of protease inhibitor in the sample by measuring the activity of the protease, characterized in that at least one of an amphoteric and a nonionic surfactant are used to prepare the substrate solution.

As used herein the terms "assay", "assaying" and "measuring the concentration" include not only absolute assessments of concentration in terms of mass per unit volume, but also other quantitative and semi-quantitative assessments of the amount or concentration of the inhibitor.

A further aspect of the invention is the use of a particular calcium content in the assay mixture. Thus, in this aspect, the invention provides a method for the assay of a protease inhibitor in a sample, comprising mixing the sample, a protease, calcium and a protease substrate, and assaying the content of protease inhibitor in the sample by measuring the activity of the protease, characterized in that, the calcium content is at least 0.15 $\mu$mol per 1 $\mu$g of protease and no more than 100 $\mu$mol per 1 ml of the sample.

The calcium may be supplied in any convenient form known in the art for such assays, e.g. as a salt, for example $CaCl_2$. As used in the present invention, the term "calcium content" refers to the concentration of calcium itself, but not to the concentration of the salt of calcium. Moreover, calcium is present in the substrate solution, the reaction solution or the like in ionic form.

Preferably, these aspects of the invention namely the use of surfactant and a particular calcium content are combined in the assay of the invention.

In one aspect, the present invention provides a method for measuring the concentration of protease inhibitor in a sample comprising mixing the sample, a protease, calcium and a substrate, and then measuring the concentration of protease inhibitor in the sample by measuring the activity of the protease, wherein the calcium content is at least 0.15 $\mu$mol per 1 $\mu$g of the protease but not more than 100 $\mu$mol per 1 ml of the sample, and wherein the substrate is used as a substrate solution containing an organic solvent, an aqueous medium, and at least one amphoteric and/or nonionic surfactant.

Preferably, the substrate is dissolved in an organic solvent, then diluted with aqueous medium (e.g. water) to prepare the substrate solution, and at least one of an amphoteric surfactant and a nonionic surfactant is added to at least one of the organic solvent and the aqueous medium.

The organic solvent may be any organic solvent, or mixture thereof known in the art for dissolving protease substrates. The aqueous medium may likewise be any suitable medium, but conveniently will be water or a buffer.

Thus, in the method of the present invention, the calcium content is specified, and specific surfactants are used with an organic solvent in dissolving the substrate. For example, when the content of calcium in the reaction solution is 0.15 μmol or more per 1 μg of trypsin, the activity of trypsin is constant. Therefore, possibilities of influence on the result by calcium present in urine can be eliminated. Furthermore, when the content of calcium in the reaction solution is 100 μmol or less per 1 ml of the urine sample, precipitates which affect the measurement are not produced. Therefore, complex operations including centrifugation are not required. Moreover, by using the above specified surfactants, the amount of an organic solvent such as DMSO to be used can be reduced, and a slightly soluble substrate such as BAPNA can be used in a sufficient amount. Accordingly, because the amount of the organic solvent is small, damage on a plastic cell can be prevented. Furthermore, because the substrate can be used in a sufficient amount, precision and reproducibility of the measurement can be improved. In addition, solubility of the substrate is improved by using the specified surfactants, so that crystallization of the substrate can be prevented.

In the method of the present invention, a buffer solution may be used in place of water in preparing the substrate solution, and it is preferable to use DMSO as the organic solvent.

In the method of the present invention, it is preferable that trypsin is used as the protease, and a compound as expressed by the following Formula I is used as the substrate:

protecting group-(amino acid residue)$_n$-p-nitroanilide;   (Formula I)

wherein n is an integer in the range of 1 to 5.

It is particularly preferable to use α-benzoyl-arginine-p-nitroanilide as the substrate. However, for example, α-benzoyl-lysine-p-nitroanilide, t-butoxycarbonyl-arginine-p-nitroanilide, or t-butoxycarbonyl-lysine-p-nitroanilide can also be used as the substrate. Furthermore, it is preferable that urine is used as the sample (although any clinical sample e.g. any body fluid or a body fluid derived sample may be used), and urinary trypsin inhibitor is the protease inhibitor.

In the method of the present invention, it is preferable that a betaine type amphoteric surfactant is used as the surfactant.

In the method of the present invention, it is preferable that at least one of 3-[(3-cholamidopropyl)dimethylammonio]-1-propanesulfonic acid and 3-[(3-cholamidopropyl)dimethylammonio]-2-hydroxy-1-propanesulfonic acid is used as the amphoteric surfactant.

In the method of the present invention, it is preferable that at least one nonionic surfactant selected from the group consisting of polyoxyethylene sorbitan monolaurate, polyoxyethylene sorbitan monooleate, polyoxyethylene (23) lauryl ether, polyoxyethylene (20) cetyl ether, polyoxyethylene (10) octylphenyl ether, polyoxyethylene nonylphenyl ether, polyoxyethylene alkyl ether, perfluoroalkyl polyoxyethylene ethanol, alkylester fluoride, polyethylene glycol mono-p-nonylphenylether, polyoxyethylene (30) octylphenyl ether, N,N-bis(3-D-gluconamidopropyl)deoxycholamide, n-octyl-β-d-thioglucoside, and sucrose monolaurate is used as the nonionic surfactant. Examples of polyoxyethylene nonylphenyl ether are Noigen EA-80, Noigen EA-120, and Noigen EA-140 (all are products of Daiichi Kogyo Seiyaku Co. Ltd.). Examples of polyoxyethylene alkyl ether are Softanol 70, Softanol 90 and Softanol 120 (all are products of Nippon Syokubai Co. Ltd.). An example of perfluoroalkyl polyoxyethylene ethanol is Fluorad FC-170C (Product of 3M). An example of alkylester fluoride is Fluorad FC-430 (Product of 3M). An example of polyoxyethylene (30) octylphenyl ether is TRITON X-305 (Product of Nacalai tesque).

In the method of the present invention, it is preferable that the content of each component in the substrate solution is as follows: 1 to 50 mmol/l of substrate, 1 to 50% by weight of organic solvent, and 0.1 to 5% by weight of surfactant.

A kit for measuring the concentration of protease inhibitor in a sample comprising a protease, a substrate and calcium, wherein the calcium content is at least 0.15 μmol per 1 μg of the protease but no more than 100 μmol per 1 ml of the sample, and wherein the substrate is dissolved in a solution which contains an organic solvent and a surfactant, the surfactant being at least one of an amphoteric surfactant and nonionic surfactant constitutes a further aspect of the present invention.

By using this measurement kit, protease inhibitors can be easily measured with high precision and high reproducibility, and without the possibility of damaging a plastic cell.

In the kit of the present invention, it is preferable that the solution in which the substrate is dissolved is prepared by dissolving the substrate in an organic solvent and diluting it with water, a surfactant is mixed in at least one of the organic solvent and the water.

In the kit of the present invention, when a reaction solution is prepared by mixing the protease, the substrate, calcium and the sample, it is preferable that the pH of the reaction solution is in the range of 5 to 9, the protease concentration in the reaction solution is in the range of 5 to 250 mg/l, and the substrate concentration in the reaction solution is in the range of 0.5 to 25 mmol/l.

In the kit of the present invention, it is preferable that DMSO is used as the organic solvent, and a substrate expressed by Formula I is used as the substrate. It is particularly preferable to use α-benzoyl-arginine-p-nitroanilide as the substrate.

In the kit of the present invention, the same surfactants as those previously described for the method of measuring the concentration of protease inhibitor of the present invention are preferably used.

Preferably the kit of the present invention comprises R1 buffer solution, R2 protease solution and R3 substrate solution as described below, the ratio of R1, R2 and R3 by volume being set in the range of R1:R2:R3=30 to 90:5 to 40:5 to 30.

R1 is prepared so that it contains at least 0.15 μmol calcium per 1 μg of the enzyme but no more than 100 μmol calcium per 1 ml of the urine sample.

R3 contains a substrate, an organic solvent and a surfactant, wherein the surfactant is at least one of an amphoteric surfactant and a nonionic surfactant.

In the kit of the present invention, calcium may be present in the R2 protease solution or in R3 substrate solution instead of in R1 buffer solution as long as it is present in the range of the above specified concentration. Indeed, the calcium may be present in all three solutions or any combination of two solutions, i.e. R1 and R2, R2 and R3 or R1 and R3. Furthermore, in the kit of the present invention, R1, R2 and R3 may be prepared either independently, or on preparation of a mixture of any two of the three types of solution and then the other solution. There are three types of combination as shown below.

(1) A mixture solution of R1 and R2+R3
(2) A mixture solution of R1 and R3+R2
(3) A mixture solution of R2 and R3+R1

In combination (3), if the enzyme reaction is controlled, for example, by adjusting pH, the enzyme and the substrate can be mixed together.

A method for dissolving a substrate comprising dissolving the substrate in an organic solvent, and diluting the mixture solution with an aqueous medium (e.g. water), wherein at least one of an amphoteric surfactant and a nonionic surfactant is added to at least one of the organic solvent and the aqueous medium constitutes a further aspect of the present invention.

This method for dissolving a substrate is not limited to the above-mentioned substrates for proteases, and it can be used for dissolving various types of substrate.

In the method for dissolving a substrate, a buffer solution may be used in place of water as in the method for measuring previously described. Furthermore, DMSO is preferably used as the organic solvent.

In the method for dissolving a substrate of the present invention, the substrate and the surfactant as specified in the method for measuring the concentration of protease inhibitor are preferably used.

In the method for dissolving a substrate of the present invention, it is preferable that the content of each component in the substrate solution is as follows: 1 to 50 mmol/l of substrate, 1 to 50% by weight of organic solvent and 0.1 to 5% by weight of surfactant.

DETAILED DESCRIPTION OF THE INVENTION

This invention will be described in detail as follows:

A method of measuring the concentration of protease inhibitor can be carried out, for example, by using a protease solution, a substrate solution prepared by using an organic solvent and a specific surfactant, and a buffer solution in which calcium is contained in a concentration within a specific range.

For example, trypsin can be used as the enzyme. The origin of the trypsin is not particularly limited, and it can be derived from, for example, bovine pancreas or porcine pancreas. Furthermore, the concentration of trypsin is determined as appropriate depending upon its specific activity or the like, and it is usually 10 to 500 mg/l, preferably 20 to 100 mg/l of the total amount of the protease solution. Furthermore, the protease solution may be adjusted to pH 2.0 to 3.0 with hydrochloric acid or a buffer solution in order to prevent autolysis of trypsin.

Examples of a protease other than trypsin which can be used in the method of the invention includes chymotrypsin. An example of a substrate for chymotrypsin is benzoyl-tyrosine-p-nitroanilide.

The surfactant in the substrate solution is at least one of an amphoteric surfactant and a nonionic surfactant as mentioned above. The surfactants as specified above are preferably used. Because 3-[(3 cholamidopropyl) dimethylammonio]-1-propanesulfonic acid (CHAPS) and 3[(3-cholamidopropyl)dimethylammonio]-2-hydroxy-1-propanesulfonic acid (CHAPSO) of amphoteric sulfobetaine type have particularly good effects in this invention, these agents are particularly preferable. In the present invention, the above-specified surfactants may be used either independently or in combination of two or more types of the surfactants.

Furthermore, a substrate expressed by Formula I is preferably used in the substrate solution as previously described, and α-benzoyl-arginine-p-nitroanilide and the like are particularly preferable.

An example of the organic solvent other than the above-mentioned DMSO is dimethylformamide (DMF).

In the present invention, an organic solvent in which a substrate is dissolved is diluted with water or with a buffer solution. In the diluting, whether water or a buffer solution is used, or what type of a buffer solution is used, is determined as appropriate depending upon, for example, the conditions of the measurement. Examples of the buffer solution are triethanolamine hydrochloride buffer, Tris-HCl buffer, phosphate buffer, glycine buffer, veronal buffer, Good's buffer and the like. The pH of these buffers are determined as appropriate depending upon, for example, the type of enzyme.

A substrate solution for use in the present invention is prepared, for example, by the following steps. First, a substrate is dissolved in an organic solvent. The concentration of the substrate is usually in the range of 1 to 50 mg to 1 ml of DMSO. On the other hand, a surfactant solution is prepared by dissolving the above-specified surfactants in water or in a buffer solution. The concentration of the surfactant is determined as appropriate depending upon, for example, the type of the surfactant to be used, and it is usually in the range of 0.1 to 5% by weight to the amount of the water or the buffer solution. Then, the organic solvent containing the substrate is diluted with the surfactant solution, usually 2 to 20-fold, preferably 10 to 20-fold, to prepare a substrate solution. The surfactant is usually mixed with the water or buffer solution, however, it may also be mixed with the organic solvent.

In this example, the calcium content in the buffer solution is in the range as mentioned above, preferably at least 0.2 μmol per 1 μg of the protease, but not more than 50 μmol per 1 ml of the sample. The pH of the buffer solution may be any value so that the pH of the reaction solution falls within the range of the above-specified value, preferably pH 7 to 8. Examples of the type of the buffer solution are triethanolamine hydrochloride buffer, Tris-HCl buffer, phosphate buffer, Good's buffer, and the like. The buffer solution is prepared by a conventional method.

For example, when urinary trypsin inhibitor is the inhibitor to be measured, the method of measuring its concentration is carried out as follows:

First, an urine sample, a buffer solution and a protease solution are mixed together. The ratio (by volume) is usually set in the following range urine sample:buffer solution:protease solution=1:5 to 10:2 to 5. Then, the mixture is incubated, usually for 1 to 5 minutes at 25° to 37° C. Then, the substrate solution is added to the mixture to cause the reaction between the enzyme and the substrate. The substrate solution is usually mixed in the range of 5 to 30% by volume to the total amount of the reaction solution. The conditions for the reaction are usually 1 to 10 minutes at 25° to 37° C. Furthermore, the pH of the reaction solution is varied depending on, for example, the type of the enzyme. When using trypsin as in this case, the pH is in the range of 7 to 8. Then, the enzyme reaction is detected by using a predetermined method to measure the enzyme activity. In this reaction, the enzyme reaction is inhibited depending upon the amount of the trypsin inhibitor in the urine sample. Accordingly, if a calibration curve is prepared in advance by using a known urinary trypsin inhibitor, the amount of the urinary trypsin inhibitor can be measured by measuring the enzyme activity. For example, when using a substrate which develops a color when the enzyme reaction takes place, the enzyme reaction may be detected by measuring the color by using a spectrophotometer or the like. Moreover, the enzyme activity can also be measured by measuring the concentration of the reaction product.

The kit of the present invention comprises, for example, R1 buffer solution, R2 protease solution and R3 substrate solution. These reagents (R1, R2, R3) can be prepared by the methods as previously described in the method for measuring the concentration of protease inhibitor, and the composition of each reagent, the proportions thereof and the like are the same as previously described. By using this kit, it is possible to conduct a simple and rapid measurement of protease inhibitors such as urinary trypsin inhibitor.

In the method for dissolving a substrate according to the present invention, examples of the substrate other than the above-mentioned substrate are Z-glycine-glycine-leucine-p-nitroanilide and succinyl-alanine-alanine-alanine-p-nitroanilide. Furthermore, the enzyme which may act on the substrate dissolved in accordance with the method of the present invention is not particularly limited, and examples of the enzyme are trypsin, chymotrypsin, elastase, subtilisin, plasmin, thorombin, kallikrein, cathepsin B, endopeptidase and urokinase.

In the method for dissolving a substrate according to the present invention, the process for performing the method and the conditions thereof and the like are the same as in the method for measuring the concentration of protease inhibitor previously described.

The invention is further described below with reference to the following non-limiting Examples.

EXAMPLE 1

R1 buffer solution, R2 protease solution and R3 substrate solution were prepared as follows:

(R1 buffer solution)

A buffer solution (pH 7.8) was prepared by a conventional method mixing the following components in purified water in the concentrations given below:

triethanolamine hydrochloride 0.2 mol/l $CaCl_2$ 0.003 mol/l (R2 protease solution)

A protease solution was prepared by a conventional method mixing the following components in the concentrations given below:

trypsin derived from bovine pancreas 50 mg/l (TYPE III 10000–13000 BAEE units/mg, Sigma)

hydrochloric acid 1.2 mmol/l (R3 substrate solution)

A required amount of BAPNA was dissolved in DMSO, and the mixture was diluted 10-fold with a solution having a predetermined surfactant concentration to prepare four types of substrate solution (a to d). Furthermore, a substrate solution as a control was prepared in the same way as described above but without adding a surfactant. These solutions were as follows:

| Substrate solution (a): | BAPNA | 500 mg |
| --- | --- | --- |
| | DMSO | 10 ml |
| | CHAPSO | 2.6 g |
| | purified water | 90 ml |
| Substrate solution (b): | BAPNA | 500 mg |
| | DMSO | 10 ml |
| | CHAPSO | 1.3 g |
| | purified water | 90 ml |
| Substrate solution (c): | BAPNA | 500 mg |
| | DMSO | 10 ml |
| | CHAPS | 2.6 g |
| | purified water | 90 ml |
| Substrate solution (d): | BAPNA | 500 mg |
| | DMSO | 10 ml |
| | CHAPS | 1.3 g |
| | purified water | 90 ml |
| Substrate solution (control): | BAPNA | 500 mg |
| | DMSO | 50 ml |
| | purified water | 50 ml |

Three types of urinary trypsin inhibitor (UTI, Miraclid: The Product of Mochida Pharmaceutical Co. Ltd.) solution having concentrations of 0 U/ml, 100 U/ml, and 200 U/ml, respectively, were prepared as samples.

Next, 0.14 ml of the sample, 1.8 ml of the buffer solution (R1) and 0.48 ml of the protease solution (R2) were mixed together and the mixture was incubated for one minute at 37° C. Then, 0.58 ml of the substrate solution (R3) was added to initiate the reaction. Then, the mixture was incubated at 37° C. and the change in absorbance (at 405 nm) for 100 seconds was measured by using a spectrophotometer to determine the relative absorbance ($\Delta O.D.$). Accordingly, calibration curves as shown in FIG. 1 were obtained.

From these results, it appears that the activity of trypsin is improved when using a specific surfactant in preparing the substrate solution. Moreover, the enzyme activity was further improved as the amount of the surfactant was increased.

Furthermore, in preparing the substrate solution in this Example, by using a specific surfactant, the amount of DMSO to be used could be reduced, also a sufficient amount of the substrate could be dissolved, and crystallization of the substrate could be prevented.

EXAMPLE 2

Urine was obtained from five healthy adults (A, B, C, D, E) as samples, and the amount of UTI was measured three times in the same way as in Example 1, using R1 buffer solution, R2 protease solution (a) as used in Example 1, and the amount of UTI was determined by using the calibration curve as prepared in Example 1. The results are shown in the following Table 1.

TABLE 1

| | A | B | C | D | E |
| --- | --- | --- | --- | --- | --- |
| measurement | 11.9 | 22.1 | 19.2 | 8.3 | 12.5 |
| value | 11.1 | 22.3 | 19.2 | 7.7 | 4.7 |
| (U/ml) | 12.9 | 21.6 | 18.7 | 3.1 | 3.7 |

The results of the Table 1 prove that reliable values for the amount of UTI were obtained by this method. Furthermore, such problems as precipitation did not occur in this method.

EXAMPLE 3

Using polyoxyethylene sorbitan monolaurate, polyoxyethylene sorbitan monooleate, polyoxyethylene (23) lauryl ether, polyoxyethylene (20) cetyl ether, polyoxyethylene (10) octylphenyl ether, Softanol 70 (Product of Nippon Syokubai Co. Ltd.), Softanol 90 (Product of Nippon Syokubai Co. Ltd.), Softanol 120 (Product of Nippon Syokubai Co. Ltd.), Noigen EA-80 (Product of Daiichi Kogyo Seiyaku Co. Ltd.), Noigen EA-120 (Product of Daiichi Kogyo Seiyaku Co. Ltd.), Noigen EA-140 (Product of Daiichi Kogyo Seiyaku Co. Ltd.), Fluorad FC-170C (Product of 3M), Fluorad FC-430 (Product of 3M), polyethylene glycol mono-p-nonylphenyl ether, TRITON X-305 (Product of Nacalai tesque), N, N-bis(3-D-gluconamidopropyl)deoxycholamide, n-octyl-β-d-thioglucoside, and sucrose monolaurate as surfactants respectively, 18 types of the substrate solution were prepared in the same way as in Example 1. The composition of the substrate solution is as follows:

| | |
|---|---|
| BAPNA | 500 mg |
| DMSO | 10 ml |
| surfactant | 2.6 g |
| purified water | 90 ml |

Next, the solubility of the substrate was examined for each substrate solution. When each of the prepared substrate solutions were allowed to stand for 24 hours at 4° C., precipitation of the substrate did not take place. The result proves that a sufficient amount of the substrate can be dissolved with DMSO of low concentration when using the above-mentioned types of nonionic surfactant. Moreover, when a control experiment was performed without adding a nonionic surfactant in this Example, crystallization of BAPNA occurred.

Next, among the substrate solutions prepared in such a way, one using polyoxyethylene sorbitan monolaurate as a nonionic surfactant was used as the R3 substrate solution. Then, after preparing a calibration curve in the same way as in Example 1, the amount of UTI in urine obtained from a subject was measured in the same way as in Example 2. The result showed that the amount of UTI was 29.0 U/ml. Precipitation did not occur in this measurement, and also the obtained value for the amount of UTI was reliable.

Finally, it is understood that the invention may be embodied in other specific forms without departing from the spirit or essential characteristics thereof. The embodiments disclosed in this application are to be considered in all respects as illustrative and not restrictive, so that the scope of the invention being indicated by the appended claims rather than by the foregoing description, and all changes which come within the meaning and range of equivalency of the claims are intended to be embraced therein.

What is claimed is:

1. A method of measuring the concentration of protease inhibitor in a sample comprising mixing the sample, a protease, calcium and a substrate, and then measuring the activity of the protease, wherein the calcium content is at least 0.15 μmol per 1 μg of the protease but no more than 100 μmol per 1 ml of the sample and wherein the substrate is used as a substrate solution containing an organic solvent, an aqueous medium and at least one amphoteric and/or nonionic surfactant.

2. The method of measuring the concentration of protease inhibitor in a sample as claimed in claim 1, wherein a buffer solution or water is used as the aqueous medium in preparing the substrate solution.

3. The method of measuring the concentration of protease inhibitor in a sample as claimed in claim 1, wherein the substrate solution is prepared by dissolving the substrate in an organic solvent, and diluting the solution with an aqueous medium, wherein the surfactant is added to at least one of the organic solvent and the aqueous medium.

4. A method of measuring the concentration of protease inhibitor in a sample as claimed in claim 1, wherein when a reaction solution is prepared by mixing the protease, the substrate, calcium and the sample, the reaction solution has a pH of 5 to 9, the protease concentration in the reaction solution is in the range of 5 to 250 mg/l, and the substrate concentration in the reaction solution is in the range of 0.5 to 25 mmol/l.

5. The method of measuring the concentration of protease inhibitor in a sample as claimed in claim 1, wherein the protease is trypsin.

6. The method of measuring the concentration of protease inhibitor in a sample as claimed in claim 5, wherein the sample is urine and the protease inhibitor is urinary trypsin inhibitor.

7. The method of measuring the concentration of protease inhibitor in a sample as claimed in claim 1, wherein the organic solvent used in preparing the substrate solution is dimethyl sulfoxide (DMSO).

8. The method of measuring the concentration of protease inhibitor in a sample as claimed in claim 1, wherein the substrate is expressed by the following Formula I:

$$\text{protecting group-(amino acid residue)}_n\text{-p-nitroanilide;} \quad \text{(Formula I)}$$

wherein n is an integer between 1 and 5.

9. The method of measuring the concentration of protease inhibitor in a sample as claimed in claim 8, wherein the substrate is α-benzoyl-arginine-p-nitroanilide.

10. The method of measuring the concentration of protease inhibitor in a sample as claimed in claim 1, wherein the amphoteric surfactant is of the betaine type.

11. The method of measuring the concentration of protease inhibitor in a sample as claimed in claim 1, wherein the amphoteric surfactant is at least one of 3-[(3-cholamidopropyl)dimethylammonio]-1-propanesulfonic acid and 3-[(3-cholamidopropyl)dimethylammonio]-2-hydroxy-1-propanesulfonic acid.

12. The method of measuring the concentration of protease inhibitor in a sample as claimed in claim 1, wherein the nonionic surfactant is at least one selected from the group consisting of polyoxyethylene sorbitan monolaurate, polyoxyethylene sorbitan monooleate, polyoxyethylene (23) lauryl ether, polyoxyethylene (20) cetyl ether, polyoxyethylene (10) octylphenyl ether, polyoxyethylene nonylphenyl ether, polyoxyethylene alkyl ether, perfluoroalkyl polyoxyethylene ethanol, alkylester fluoride, polyethylene glycol mono-p-nonylphenylether, polyoxyethylene (30) octylphenyl ether, N,N-bis(3-D-gluconamidopropyl) deoxycholamide, n-octyl-β-d-thioglucoside, and sucrose monolaurate.

13. The method of measuring the concentration of protease inhibitor in a sample as claimed in claim 1, wherein the content of each component in the substrate solution is as follows: 1 to 50 mmol/l of substrate, 1 to 50% by weight of organic solvent, and 0.1 to 5% by weight of surfactant.

14. A kit for measuring the concentration of protease inhibitor in a sample comprising a protease, a substrate and calcium, wherein the calcium content is at least 0.15 μmol per 1 μg of the protease but no more than 100 μmol per 1 ml of the sample, and wherein the substrate is dissolved in a solution which contains an organic solvent, an aqueous medium and at least one amphoteric and/or nonionic surfactant.

15. The kit as claimed in claim 14, wherein a buffer solution or water is used as the aqueous medium in preparing the substrate solution.

16. The kit as claimed in claim 14, wherein the substrate solution is prepared by dissolving the substrate in an organic solvent, and diluting the solution with an aqueous medium, wherein the surfactant is added to at least one of the organic solvent and the aqueous medium.

17. The kit as claimed in claim 14, wherein when a reaction solution is prepared by mixing the protease, the substrate, calcium and the sample, the reaction solution has a pH of 5 to 9, the protease concentration in the reaction solution is in the range of 5 to 250 mg/l, and the substrate concentration in the reaction solution is in the range of 0.5 to 25 mmol/l.

18. The kit as claimed in claim 14, wherein the protease is trypsin.

19. The A kit as claimed in claim 18, wherein the sample is urine and the protease inhibitor is urinary trypsin inhibitor.

20. The kit as claimed in claim 14 comprising a buffer solution (R1), a protease solution (R2), and a substrate solution (R3), the ratio of R1, R2 and R3 by volume being in the range of R1:R2:R3=30 to 90:5 to 40:5 to 30, wherein (R1) is prepared so that it contains at least 0.15 $\mu$mol calcium per 1 $\mu$g of the protease but no more than 100 $\mu$mol calcium per 1 ml of the sample and wherein (R3) contains a substrate, an organic solvent and a surfactant, wherein the surfactant is at least one of an amphoteric surfactant and a nonionic surfactant.

21. The kit as claimed in claim 14, wherein the organic solvent used in preparing the substrate solution is dimethyl sulfoxide (DMSO).

22. The A kit as claimed in claim 14, wherein the substrate is expressed by the following Formula I:

protecting group-(amino acid residue)$_n$-p-nitroanilide;  (Formula I)

wherein n is an integer between 1 and 5.

23. The kit as claimed in claim 22, wherein the substrate is α-benzoyl-arginine-p-nitroanilide.

24. The kit as claimed in claim 14, wherein the amphoteric surfactant is of the betaine type.

25. The kit as claimed in claim 14, wherein the amphoteric surfactant is at least one of 3-[(3-cholamidopropyl)dimethylammonio]-1-propanesulfonic acid and 3-[(3-cholamidopropyl)dimethylammonio]-2-hydroxy-1-propanesulfonic acid.

26. The kit as claimed in claim 14, wherein the nonionic surfactant is at least one selected from the group consisting of polyoxyethylene sorbitan monolaurate, polyoxyethylene sorbitan monooleate, polyoxyethylene (23) lauryl ether, polyoxyethylene (20) cetyl ether, polyoxyethylene (10) octylphenyl ether, polyoxyethylene nonylphenyl ether, polyoxyethylene alkyl ether, perfluoroalkyl polyoxyethylene ethanol, alkylester fluoride, polyethylene glycol mono-p-nonylphenylether, polyoxyethylene (30) octylphenyl ether, N,N-bis(3-D-gluconamidopropyl) deoxycholamide, n-octyl-β-d-thioglucoside, and sucrose monolaurate.

27. The kit as claimed in claim 14, wherein the content of each component in the substrate solution is as follows: 1 to 50 mmol/l of substrate, 1 to 50% by weight of organic solvent, and 0.1 to 5% by weight of surfactant.

28. A method of preparing a protease substrate solution comprising dissolving a protease substrate in an organic solvent to form a first solution and diluting the first solution with an aqueous medium, wherein at least one of an amphoteric surfactant and a nonionic surfactant is added to at least one of the organic solvent and the aqueous medium.

29. The method of dissolving a protease substrate as claimed in claim 28, wherein the aqueous medium is a buffer solution or water.

30. The method of dissolving a protease substrate as claimed in claim 28, wherein the organic solvent used in preparing the protease substrate solution is dimethyl sulfoxide (DMSO).

31. The method of dissolving a protease substrate as claimed in claim 28, wherein the protease substrate is expressed by the following Formula I:

protecting group-(amino acid residue)$_n$-p-nitroanilide;  (Formula I)

wherein n is an integer between 1 and 5.

32. The method of dissolving a protease substrate as claimed in claim 31, wherein the substrate is α-benzoyl-arginine-p-nitroanilide.

33. The method of dissolving a protease substrate as claimed in claim 28, wherein the amphoteric surfactant is of the betaine type.

34. The method of dissolving a protease substrate as claimed in claim 28, wherein the amphoteric surfactant is at least one of 3-[(3-cholamidopropyl)dimethylammonio]-1-propanesulfonic acid and 3-[(3-cholamidopropyl)dimethylammonio]-2-hydroxyl-1-propanesulfonic acid.

35. The method of dissolving a protease substrate as claimed in claim 28, wherein the nonionic surfactant is at least one selected from the group consisting of polyoxyethylene sorbitan monolaurate, polyoxyethylene sorbitan monooleate, polyoxyethylene (23) lauryl ether, polyoxyethylene (20) cetyl ether, polyoxyethylene (10) octylphenyl ether, polyoxyethylene nonylphenyl ether, polyoxyethylene alkyl ether, perfluoroalkyl polyoxyethylene ethanol, alkylester fluoride, polyethylene glycol mono-p-nonylphenylether, polyoxyethylene (30) octylphenyl ether, N,N-bis(3-D-gluconamidopropyl) deoxycholamide, n-octyl-p-d-thioglucoside, and sucrose monolaurate.

36. The method of dissolving a protease substrate as claimed in claim 28, wherein the content of each component in the protease substrate solution is as follows: 1 to 50 mmol/l of protease substrate, 1 to 50% by weight of organic solvent, and 0.1 to 5% by weight of surfactant.

* * * * *